United States Patent [19]

Michaels

[11] 4,145,436

[45] Mar. 20, 1979

[54] ANTIMICROBIAL COMPOSITIONS AND METHOD FOR USING SAME

[76] Inventor: Edwin B. Michaels, Gregory Ct., East Norwalk, Conn. 06855

[21] Appl. No.: 849,031

[22] Filed: Nov. 7, 1977

[51] Int. Cl.$^2$ ............................................. A61K 31/415
[52] U.S. Cl. ................................. 424/273 R; 424/320; 424/325; 252/106
[58] Field of Search ................. 252/106; 424/273, 316, 424/325, 320

[56] References Cited

U.S. PATENT DOCUMENTS 3,484,523   12/1969   Findlan et al. .................... 424/329

OTHER PUBLICATIONS

Kirk–Othmer Encyc. of Chem. Tech., 2nd Ed., vol. 19 (1969), pp. 555–559, 561–566, 575–577.

Primary Examiner—V. D. Turner

[57] ABSTRACT

There are provided antimicrobial compositions of the low toxicity having enhanced activity against gram positive and gram negative bacteria as well as fungi or protozoa and consists essentially of:
(a) an alkylimidazolium betaine in amounts up to 40 parts, by weight, and
(b) an alkyl-N,N-dimethylamine oxide, an alkyl-N,N-dihydroxyethylamine oxide, or an acrylamido t-amine oxide in amounts up to 40 parts, by weight.

The composition exhibits skin degerming, cleansing, and deodorizing properties and, particularly, its use exhibits long term inhibition of body odor.

11 Claims, No Drawings

ANTIMICROBIAL COMPOSITIONS AND METHOD FOR USING SAME

The present invention relates to antimicrobial compositions of enhanced efficacy and safety. More particularly, the invention relates to antimicrobial compositions having low toxicity and broad spectrum, antimicrobial activity consisting essentially of certain surfactants which individually have limited antimicrobial use. Still more particularly, the invention is concerned with antimicrobial compositions of enhanced gram positive and gram negative activity consisting essentially of in admixture:

(a) an alkylimidazolium betaine from 0.1 to 40.0 parts, by weight, and (b) an alkyl-N,N-dimethylamine oxide, an acylamido t-amine oxide, or an alkyl-N,N-dihydroxyethl amine oxide from 0.1 to 40.0 parts, by weight.

The compositions of the present invention, useful as topical germicides, exhibit sustained periods of antimicrobial activity, particularly in the control of body odor, over a wide pH range, namely, from about pH 4 to about pH 9.5.

It is known that a method for the control of body odor is to thoroughly wash the body with soap. However, the microbial flora of the skin are so prolific that distinctive malodors tend to return within several hours after washing. To provide longer periods of protection, there have been developed compositions which contain either an astringent, such as aluminum chlorohydrate, that inhibits aporcrine and eccrine gland secretions or an antimicrobial agent, such as hexachlorophene or or trichlorocarbanilamide. Unfortunately, an astringent composition has limited value, since it has little or no control of microbial decomposition of debris and uncontrolled secretions and, where there is control of secretions by antimicrobials, such use suffers from a severe shortened period to obtain effective control of body odor. Nonetheless, such latter antimicrobial compositions of shortened time effectiveness have enjoyed widespread use. In this connection, however, there have been recent investigations into topical and systemic toxicity of the hereinabove named germicides. These investigations have led to severe restrictions, for instance, on the utilization of hexachlorophene and the recognition of the dangers of other germicides. Further, astringents have only limited utility usually due to the harsh or corrosive action on skin, particularly, on people who have sensitive skin. If a safe and effective antimicrobial composition of low toxicity could be provided which would inhibit the development of body odor for relatively long periods of time for at least 24 hours, or longer, such a composition would satisfy a well recognized need in the art.

It is a principal object of the invention to provide a composition of enhanced efficacy and safety which possesses broad spectrum, antimicrobial activity in combating body odor as well as a variety of topical infections. It is a further object of the invention to provide an antimicrobial composition comprising at least an alkylimidazolium betaine surfactant and an alkyl-N, N-dimethylamine oxide, an acylamido t-amine oxide, or an alkyl-N, N-dihydroxyethylamine oxide, adjusted to a pH of about 4.0 to about 9.5 so as to control gram positive bacteria, gram negative bacteria, fungi, and protozoa when topically applied. Other objects and advantages will become apparent from a consideration of the ensuing description.

According to the invention, there are provided antimicrobial compositions consisting essentially of a mixture of (a) an alkylimidazolium betaine and (b) an alkyl-N,N-dimethylamine oxide, or an alkyl-N,N-dihydroxyethylamine oxide, or an acylamido t-amine oxide. The compositions are prepared by admixing the same at a temperature ranging from about 25° C. to 80° C. in a substantially aqueous or non-aqueous environment and adjusted to a pH of about 4.0 to about 9.5 to provide a substantially uniform homogeneous composition having both enhanced broad spectrum antimicrobial activity and low toxicity.

In general, a first component, namely, an alkylimidazolium betaine surfactant employed as a nonionizing zwitterion can be written as:

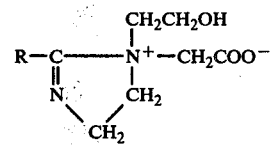

where R is a higher alkyl having from 10 to 17 carbon atoms. Illustrative of such alkylimidazolium betaines are: 1-hydroxyethyl-1-carboxymethyl-2-decylimidazolium betaine; 1-hydroxyethyl-1-carboxymethyl-2-dodecylimidazolium betaine; 1-hydroxyethyl-1-carboxymethyl-2cocoimidazolium betaine; 1-lhydroxyethyl-14-carboxymethyl-2-stearylimidazolium betaine; 1-hydroxyethyl-1-carboxymethyl-2-oleylimidazoliumbetaine; or mixtures of the same.

A second component, namely, the (1) alkyl-N,N-dimethylamine oxide, (2) alkyl-N,N-dihydroxyethylamine oxide, or (3) acylamido t-amine oxide component of the aforementioned mixture, respectively, has the structure:

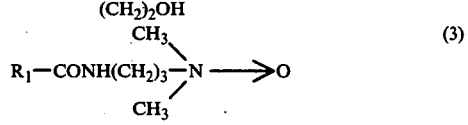

where $R_1$ in each is a higher alkyl from 10 to 18 carbon atoms, as for instance, a radical such as decyl, undecyl, lauryl, tridecyl, myristyl, cetyl, stearyl, isostearyl, oleyl or mixtures of the same. Exemplary of the latter amine oxides ar: decyl-N, N-dimethylamine oxide, lauryl-N,N-dimethylamine oxide, stearyl-N, N-dimethylamine oxide, oleyl-N,N-dimethylamine oxide, cocoamido-trimethylene-N,N-dimethylamine oxide, stearylamido-trimethylene-N,N-dimethylamine oxide, decyl-N,N-dihydroxyethylamine oxide, lauryl-N,N-dihydroxyethylamine oxide, coco-N,N-dihydroxyethylamine oxide, stearyl-N,N-dihydroxyethylamine oxide, oleyl-N,N-dihydroxyethy lamine oxide, and mixtures of the same.

In practice, each of the components of the overall composition ranges widely from 0.1 part to 40.0 parts and, preferably, from 1 to 20 parts, all by weight. There is added to the mixture an inert polar solvent, such as water or a lower monohydric aliphatic alcohol, water being preferred, for a total of at least 100 parts, and maintained at a pH ranging from about 4 to about 9.5. Where water is employed, small amounts of a lower alkyl alcohol, such as ethanol or propanol, may also be added to provide ease in formulation. The pH of the total composition may be adjusted to the requisite pH by methods well known in the art. The composition can be employed as a solution, as a spray in a suitable propellant, such as an aerosol spray utilizing commercially available "Freon" fluorocarbon, butane or equivalent propellant. Alternatively, the composition can be prepared as a solid cake when admixed with suitable fillers.

Advantageously, the compositions of the present invention possesses an extremely low toxicity, exhibiting at use concentration an $LD_{50}$ in Swiss-Webster mice having a value greater than 15 grams per kilogram by oral administration which is considered to be non-toxic. Further, there is observed a lack of primary irritation to the skin and less eye irritation as compared with ordinary soap.

In general, the compositions of the present invention can be used to treat a variety of microbial infections in a wide variety of concentrations. For instance, when bactericidally effective amounts containing the combined components ranging from 0.1 to 40 parts, by weight, and preferably from 1 to 20 parts, by weight, of the active components per 100 parts, by weight, of the overall mixture, are applied to infected or uninfected wounds, including either pyogenic or burn wounds, rapid healing is observed. The compositions are capable of relieving ear infections where solutions of the compositions of the invention are employed as an ear douche. Dandruff, crotch itch, athlete's foot, and acne caused by mild microbial infections are capable of being eliminated. Significantly, the compositions of the present invention when preferably employed as a general personal body wash, body odors particularly in the axillary, anal and genital areas are inhibited for periods in excess of 24 hours, and longer. Hence, the compositions are capable of use in a wide variety of preparations involving the cosmetic, medical and veterinary areas.

The micoorganisms causing the hereinabove described conditions are generically bacteria, fungi or protozoa. Illustrative bacteria are *Staphylococcus aureus, Staphylococcus epidermidis, Proteus vulgaris, Escherichia coli, Bacillus subtilis, Streptococcus pyogenes, Salmonella tyhimirium, Pseudomona aeriginosa, Klebsiela pneumoniae* and *Shigella flexniri*. Exemplary fungi include *Candida albicans, Trichophyton mentagrophytes* and *Saccharomyces cerevisiae*. Typical protozoa species, such as *Trychomonas vaginalis* and *Entamaeba histolytica*, are also adversely affected when subjected to the compositions of the present invention.

In order to facilitate a further understanding of the invention, the following examples are presented primarily for purposes of illustrating certain more specific details thereof. The invention is not to be deemed as limited thereby except as defined in the claims. Unless otherwise noted, as parts and percentages are by weight.

EXAMPLE 1

In this in vivo example, several compositions are employed and used as a body wash. These compositions are set forth in the table below.

Thirteen panels each consisting of five men and five women as subjects are selected and supplied with samples of the compositions as defined below and a soap control. After twenty-four (24) hours have elapsed since the panel members' last washing, each is instructed to wash, noting particularly the axillary odor before and after washing.

The bacteria noted on the skin of the panel members in this example which are among those reported responsible for body odor are *Staphylococcus aureus, Staphlococcus epidermidis, Proteus vulgaris* and *Escherichia coli*. The panel members are then monitored and examined during the next twenty-four (24) hours, and longer, for the time span when typical body odors develop. These times are then noted and recorded in Table I below.

TABLE I

| Panel No. | Sole composition used by each panelist | Average Elapsed Time Body Odor Is Detected (hours) |
|---|---|---|
| 1. | 1-Hydroxyethyl-1-carboxymethyl-2-cocoimidazolium betaine (6%) plus cocoamido-N,N-dimethylamine oxide (6%) in distilled water, citric acid(0.55%) in distilled water at a pH=5. | 72 |
| 2. | 1-Hydroxyethyl-1-carboxymethyl-2-cetylimidazolium betaine -4%, plus 70/30 myristyl/palmitic-N,N-dimethylamine oxide-6% in distilled water, adjusted to pH=5. with acetic acid. | 60 |
| 3. | 1-Hydroxyethyl-1-carboxymethyl-2-oleylimidazolium betaine-6% plus Oleyl-N,N-dimethylamine oxide-6% in distilled water, adjusted to pH=5.5 with citric acid. | 54 |
| 4. | 40/30 Myristyl/palmitic-N,N-dihydroxyethylamine oxide-6% + 1-hydroxyethyl-1 carboxymethyl-2-cocoimidazolium betaine-6% in distilled water, adjusted to a pH=8.5. | 96 |
| 5. | Cocoamido-N,N-dimethylamine oxide(12%) in distilled water-pH adjusted to 7. | 8 |
| 6. | Cocoamido-N,N-dimethylamine oxide(12%) in distilled water - pH adjusted to 5.4 with citric acid. | 10 |
| 7. | 1-Hydroxyethyl-1-carboxymethyl-2-cocoimidazolium betaine(12%) in distilled | |

TABLE I-continued

| Panel No. | Sole composition used by each panelist | Average Elapsed Time Body Odor Is Detected (hours) |
|---|---|---|
| | water - pH adjusted to 8.2. | 12 |
| 8. | 1-Hydroxyethyl-1-carboxymethyl-2-cocoimidazolium betaine (12%) in distilled water - pH adjusted to 5.4 with citric acid. | 12 |
| 9. | 1-Hydroxyethyl-1-carboxymethyl-2-cocoimidazolium betaine(6%)+coco-N,N-dimethylamine oxide(6%) in distilled water adjusted to pH of 10.4. | 12 |
| 10. | 70/30 Myristyl/palmitic-N,N-dimethylamine oxide(12%) in distilled water-pH adjusted to 5.5 with citric acid. | 12 |
| 11. | Decyl-N,N-dimethylamine oxide(12%) in distilled water-pH adjusted to 5.2 with acetic acid. | 8 |
| 12. | 70/30 Myristyl/palmitic-N,N-dimethylamine oxide(6%) + lauryl-N,N-dimethylamine oxide-(6%) in distilled water, adjusted to a pH of 5.2 with citric acid. | 10 |
| 13. | Ivory Soap | 6 |

In the above table, it can be clearly seen that the two component compositions of the present invention cause a marked improvement in body odor inhibition as compared to a one component system or even a two component system at a pH above 9.5. Compositions adjusted to a pH below 4 could not be employed, since they are too corrosive and harsh to the skin of the panelists.

EXAMPLE 2

The relationship between antimicrobial activity for the bacteria enumerated above and control of body odor is determined by subjecting some panel members to Example 1 to washing tests employing typical compositions of Example 1. There are obtained the density of microbes comprising *Staphylococcus aureus, Staphylococcus epidermidis, Proteus vulgaris,* and *Escherichia coli* in the axillary area of each panelist by using a 3 inch in diamter Rodac plate comprising Tryptose soy agar with Tween ® 80 and lecithin to neutralize any residual test composition. The panelist presses the plate for 30 seconds to the axillary area of the armpit. The plates are then incubated to 37° C. for 24 hours and the number of microorganisms as colonies are counted. The density of the colonies per square inch is next calculated.

The data obtained are noted in the table below and are the average values of the subjects treated.

TABLE II

| Composition of Example 1 | Approximate No. of colonies 0 hours after washing | Approximate No. of colonies 12 hours after washing | Approximate No. of colonies 24 hours after washing | Approx. No. of colonies 48 hours after washing |
|---|---|---|---|---|
| 1 | 400 | 900 | 1300 | 2000 |
| 2 | 300 | 350 | 1100 | 1000 |
| 5 | 1000 | 2300 | TNC* | TNC* |
| 6 | 1200 | 2500 | TNC | TNC |
| 7 | 1000 | 2350 | TNC | TNC |
| 8 | 1100 | 2450 | TNC | TNC |
| 9 | 1200 | 2500 | TNC | TNC |

*TNC means too numerous to count-The density is greater than 3000 colonies per square inch.

EXAMPLE 3

There are admixed in a suitable vessel at 40° C. 1-hydroxyethyl-1-carboxymethyl-2-stearylimidazolium betaine (6.25 gm.), coco-N,N-dimethylamine oxide (13 gm.), citric acid (4.5 gm.) and 125 gm. of distilled water. The pH of the mixture when diluted to 0.5% actives is equal to 5.0.

The mixture is tested as a body shampoo on a panel of five males and five female adults and after 60 hours subsequent to washing, the panel reports no evidence of body odor in the axillary areas.

EXAMPLE 4

A mixture of 1-hydroxyethyl-1-carboxymethyl-2-stearylimidazolium betaine (6.5 gms.), coco-N,N-dimethylamine oxide (13 gms.), acetic acid (4.5 gms.), and 66 gms. of water, formed at 50° C. and having a pH on dilution is equal to 5.1, is employed as a body wash as in Example 3 above. Body odor is absent after seventy-two (72) hours.

Substituting hydrochloric acid for acetic acid in the above mixture, similar results are noted.

EXAMPLE 5

There are admixed 1-hydroxyethyl-1-carboxymethyl-2-cetylimidazolium betaine (2.5 gms.), myristyl-N,N-dimethylamine oxide (5.5 gms.), and 87 gms. of water. The mixture is heated to 60° C. and the pH determined on dilution is 8.0.

As in Example 4 above, the mixture is used as a body wash to determine axillary and pubic body odors. After 72 hours subsequent to washing, no body odor is detected. Moreover, panel members with dandruff report complete control of dandruff after two days' use when washing once each day with the above composition.

EXAMPLE 6

A mixture of 1-hydroxythyl-1-carboxymithyl-2-laurylimidazolium betaine (5.2 gms.), 70/30 myristyl/palmitic-N,N-dimethylamine oxide mixture (5.5 gms.) citric acid (0.7 gms.) and water 108 gms.) is heated to 35° C. The pH of the diluted solution is 5.4 and is used as a body wash. No body odor is detected for seventy-two (72) hours after washing.

EXAMPLE 7

There are added at 30° C. 6.2 gms. of 1-hydroxyethyl-1-carboxymethyl-2cocoimidazolium betaine, 6.2 gms. of 70/30 myristyl/palmitic-N,N-dimethylamine oxide, 5. gms. of isopropanol, 0.7 gm. of citric acid, and 92 gms. of water. Upon dilution, the pH measured equals 5.5.

The mixture is used as a body shampoo and controls body odor in all panel members for 48 hours after washing.

EXAMPLE 8

There are admixed at 75° C. in a suitable vessel 3.25 gms. of 1-hydroxyethyl-1-carboxymethyl-2-cetylimidazolium betaine, 3.25 gms. of 1-hydroxyethyl-1-carboxymethyl-2-cocoimidazolium betaine, 6.5 gms. of 70/30 myristyl/palmitic-N,N-dimethylamine oxide, 1 gm. of isopropanol, 1.2 gms. of citric acid, and 84.8 gms. of water. There is obtained a solution having a pH=5.

The composition, when used normally as a body wash, controls odor for more than 96 hours after washing.

EXAMPLE 9

This example illustrates the formulation of a solid composition. A solid cake is prepared by blending 32 gms. of 1-hydroxyethyl-1-carboxymethyl-2-stearylimidazolium betaine, 32 gms. of myristyl/palmitic-N,N-dimethylamine oxide, 20 gms. of isopropanol, 40 gms. of water, 6.3 gms. of citric acid and 50 grams of Carbowax# polyethylene glycol having a molecular weight of 10,000. This mixture is vigorously stirred and heated to a temperature of 80° C. Resultant composition is then dried by evaporation and cooled. There is recovered a waxy solid product having a pH equal to 5.0 at a 0.5% aqueous concentration.

The solid composition is employed as solid detergent for washing and controls body odor for 48 hours after washing.

EXAMPLE 10

In this example there is prepared a spray composition. There are admixed 0.1 gm. 1-hydroxyethyl-1-carboxymethyl-2-cetylimidazolium betaine, 0.1 gm. coco-N,N-dimethylamine oxide, 10 gms. isopropanol, and 0.02 gm. of citric acid. The mixture is heated to 40° C., cooled, and admixed with 100 gms. of liquefied butane in a suitable container.

Resultant composition is sprayed under the armpits of several panelists. Each reports underarm odor control for at least 48 hours after use.

EXAMPLE 11

There are added to a suitable mixing vessel with stirring 8 gms. of 1-hydroxyethyl-1-carboxymethyl-2-cocoimidazolium betaine, 8 gms. of 1-hydroxyethyl-1-carboxyethyl-2-stearylimidazolium betaine, 16 gm.s of 70/30 myristyl/palmitic-N,N-dimethylamine oxide, 3.3 gms. of citric acid and q.s. to 250 gms. of water. Resultant mixture is stirred vigorously and heated to 60° C. for 15 minutes. Upon cooling, the pH of the mixture is found to possess a pH equal to 4.7.

Resultant composition is employed as a body wash following the procedure of Example 2 above. After 12 hours, it is found by each of five panelists that no body odor is detected and a bacterial count of 190 colonies per square inch is obtained. After 36 hours, no body odor is reported and the bacterial count rose to 600 colonies per square inch.

EXAMPLE 12

This example illustrates the effect of using a typical composition of the invention on infected wounds.

Ten shaved Guinea pigs are incised. Two incisions are effected in each animal. These are approximately 4 centimeters in length. The two incisions are located on each animal parallel to the vertebral column, and extend through the dermal layer to the fascia. Each of the wounds is next innoculated with 0.1 milliliter of an 18 hour broth containing $10^8$ *Staphylococcus aureus* per milliliter. To one of the so innoculated wounds on each animal is added 0.1 ml. of the composition of Example 8 as a 13% solution and to the other wound is added 0.1 ml. of an isotonic saline solution as a control. The wounds are then bandaged.

After 48 hours, the bandages are removed and the wounds are examined. They are swabbed for a culture of the remaining *Staphylococcus aureus* microorganisms.

It is observed that all the wounds treated with the composition of Example 8 has closed and were healing absent any substantial erytherma or reddening. Further, eight of the 10 wounds showed negative cultures. Of the wounds treated with the control composition (i.e., the isotonic saline solution) seven of the 10 wounds remain open, four of the latter 10 show bleed-on palpation, and all saline treated wounds show positive cultures of *Staphylococcus aureus* on swabbing and culturing.

EXAMPLE 13

This example illustrates the effect of a typical composition in treating a systemic infection caused by burns.

Following the procedure outlined by Stieritz et al. in the Journal of Infectious Diseases, Vol. 131, No. 6 (June 1975), twenty female CFI mice (Carwroth Farms, Wilminton, Mass.) are shaved and anesthesized. Each is subjected to a non-lethal burn over 20% of the body surface for 8 seconds and exposed to 0.2 ml. of *Pseudomonas aeruginosa* M-2 at a concentration of $10^4$/ml.

Ten burned, infected mice are untreated and are taken as the controls. They are observed for 14 days. Three of the 10 mice died by day seven and are necropsied. Each shows positive cultures in the heart, spleen, and liver for the test organism.

Ten burned, infected mice are treated 10 minutes after receiving the burn with 0.3 ml. of the composition of Example 8 in a spray form employing "Freon" as the propellant. The burned infected mice which are so treated are also observed for 14 days. However, none of the animals succumbed and show no signs of infection. The wounds healed normally.

EXAMPLE 14

This example illustrates the in vitro effect on a variety of microorganisms employing the composition of Example 8, above.

The microorganisms set forth in the table below are incubated for 24 hours and diluted with an isotonic saline solution to obtain a standard suspension of $10^8$ organisms per milliter.

The composition of Example 8 (i.e., germicide) is diluted with distilled water in 10 milliliter tubes to contain concentrations from 1.3 micrograms per milliliter to 130,000 micrograms per milliliter. Thereafter, 0.1 ml. of the standard suspension of the oganisms is innoculated into the various dilutions of the diluted germicide, stirred, and after 1, 5, and 15 minute exposures are streaked on Letheen agar plates. As the Letheen ("Tween" 80-lecitin agar) inactivates the germicide, the lack of growth of the microorganisms on the streaked plates evidences germicidal activity of the test solutions. Each of the streaked plates is incubated for 48 hours at 35° C. and examined for evidence of surviving organisms.

As indicated in Table III below, the numbers indicate the concentration expressed in micrograms per milliliter at which there is a complete absence or organisms, indicating total effectiveness of the combined components or germicide, namely, 100% kill. Each of the numbers ranging from 1.3 to 13,000 in micrograms per milliliter is termed the minimum cidal concentration (micrograms/ml.).

The test solutions are controlled by omitting the germicide while innoculating the microorganisms into distilled water and plating the resultant solution onto Letheen agar. In all instances there is noted positive growth of 4+, i.e., the colonies are too numerous to count.

Table III

| Microorganism | Minimum Cidal Concentration in Micrograms/ml. After exposure in minutes | | |
|---|---|---|---|
| | 1 min. | 5 min. | 15 min. |
| E.coli | 13 | 13 | 13 |
| K.pneumoniae | 130 | 13 | 13 |
| Salmonella typhimirium | 130 | 13 | 13 |
| Shigella Sonnie | 13 | 1.3 | 1.3 |
| P. mirabilis | 1300 | 130 | 130 |
| Serratia maracens | — | 13000 | 130 |
| Mima polymorpha | 13 | 13 | 1.3 |
| Heilla vaginicola | 130 | 13 | 130 |
| Pseud. aeruginosa | 130 | 130 | 13 |
| Staph. aureus | 13 | 13 | 13 |
| Staph. epidermidis | 130 | 13 | 13 |
| B-Strep. | 130 | 130 | 13 |
| Strep. viridans | 130 | 130 | 130 |
| B. subtilis | 1300 | 1300 | 1300 |
| Candida albicans | 13 | 13 | 13 |

Similar results are noted when employing the composition of Example 3 above.

EXAMPLE 15

Following the procedure of Example 14 in every detail except that 1-hydroxyethyl-1-carboxymethyl-2-cetylimidazolium betaine, 70/30 myristyl/palmitic-N,N-dimethylamine oxide mixture, and a mixture of approximately 50/50 -1-hydroxyethyl-1-carboxymethyl-2-cetylimidazolium betaine and the amine oxide is employed individually in lieu of the composition of Example 8. Each of the components or mixture is adjusted to a pH of 5.4 with citric acid. The microorganism selected is Staphylococcus aureus.

It is found that the minimum cidal concentration in micrograms/ml. for the betaine alone is 50, for the amine oxide it is 500 and for the mixture of the betaine and amine oxide it is 5.

This indicates that, in vitro, the mixture of components of the present invention exhibits at least a 10 fold decrease in minimum cidal concentration as contrasted to the utilization of each of the components of the mixture.

EXAMPLE 16

The procedure of Example 14 is repeated in every detail except that 1-hydroxyethyl-1-carboxymethyl-2-cocoimidazolium betaine, cocoamido-N,N-dimethylamine oxide and a mixture of approximately 50/50 1-hydroxyethyl-1-carboxymethyl-2-cocoimidazolium betaine and cocoamido-N,N-dimethylamine oxide are utilized individually in lieu of the composition of Example 8, above. Each of the components and the mixture is adjusted to a pH of 5.4 with citric acid and the microorganism selected to E.Coli.

In this in vitro test, it is found that the minimum cidal concentration of micrograms per milliliter for the betaine is 50, for the amine oxide it is more than 5000, and for the mixture of the two it is 5. Clearly, there is indicated for the mixture of components of the present invention at least a 10-fold decrease against a gram negative organism in the minimum cidal concentration as contrasted to each of the individual components of the mixture.

I claim:

1. A broad spectrum, antimicrobial composition having both a pH ranging from about 4 to about 9.5 and low toxicity which consists essentially of:
(a) from 0.1 to 40 parts, by weight, of a higher alkylimidazolium betaine, said betaine having the structure:

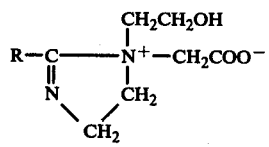

where R is higher alkyl or mixed higher alkyl of from 10 to 18 carbon atoms, and
(b) from 0.1 to 40 parts, by weight, of a higher alkyl-N, N-dimethylamine oxide, a higher alkyl-N,N-dihydroxyethylamine oxide, or an acylamido t-amine oxide having the respective structure:

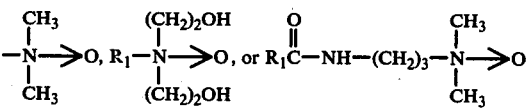

where $R_1$ is a higher alkyl or mixed higher alkyl of from 10 to 18 carbon atoms.

2. The composition according to claim 1, wherein from 1 to 20 parts of each of said betaine and amine oxide are present.

3. The composition according to claim 1, wherein the alkyl-N-betaine is 1-hydroxyethyl-1-carboxymethyl-2-cocoimidazolium betaine.

4. The composition according to claim 1, wherein the alkyl-N-betaine is 1-hydroxyethyl-1-carboxymethyl-2-stearylimidazolium betaine.

5. The composition according to claim 1, wherein the higher alkylamine oxide is stearyl-N,N-dimethylamine oxide.

6. The composition according to claim 1, wherein the higher alkylamine oxide is myristyl/palmitic-N,N-dimethylamine oxide.

7. The composition according to claim 1, wherein the higher alkylamine oxide is coco-N,N-dimethylamine oxide.

8. The composition according to claim 1, wherein the higher alkylamine oxide is stearyl-N,N-dihydroxyethylamine oxide.

9. The method for inhibiting the growth of microorganisms selected from the class consisting of bacteria, fungi and protozoa which comprises: applying thereto an antimicrobially effective amount of the composition of claim 1.

10. The method according to claim 9, wherein the growth of microorganisms is inhibited in incised wounds.

11. The method according to claim 9, wherein the growth of microorganisms is inhibited in pyogenic wounds.

* * * * *